United States Patent
Zheng et al.

(10) Patent No.: US 11,796,443 B2
(45) Date of Patent: Oct. 24, 2023

(54) METHOD FOR ISOLATING PLACENTAL TROPHOBLAST CELLS FROM CERVICAL EXFOLIATED CELLS OF PREGNANT WOMAN

(71) Applicants: GUANGZHOU HYBRIBIO MEDICINE TECHNOLOGY LTD., Guangdong (CN); GUANGDONG HYBRIBIO BIOTECH CO., LTD., Guangdong (CN)

(72) Inventors: Yan Zheng, Guangdong (CN); Jiayan Ma, Guangdong (CN); Xiaowei Feng, Guangdong (CN); Mengyu Liu, Guangdong (CN); Peixuan Chen, Guangdong (CN); Zhisheng Guan, Guangdong (CN); Longxu Xie, Guangdong (CN); Yiyuan Ge, Guangdong (CN)

(73) Assignees: GUANGZHOU HYBRIBIO MEDICINE TECHNOLOGY LTD., Guangdong (CN); GUANGDONG HYBRIBIO BIOTECH CO., LTD., Guangdong (CN)

( * ) Notice: Subject to any disclaimer, the term of this patent is extended or adjusted under 35 U.S.C. 154(b) by 0 days.

(21) Appl. No.: 18/009,740

(22) PCT Filed: Mar. 16, 2022

(86) PCT No.: PCT/CN2022/081234
§ 371 (c)(1),
(2) Date: Dec. 12, 2022

(87) PCT Pub. No.: WO2022/242285
PCT Pub. Date: Nov. 24, 2022

(65) Prior Publication Data
US 2023/0228667 A1    Jul. 20, 2023

(30) Foreign Application Priority Data
May 20, 2021 (CN) .......................... 202110549947.8

(51) Int. Cl.
*G01N 15/14* (2006.01)
*C12N 5/073* (2010.01)

(52) U.S. Cl.
CPC ........... *G01N 15/14* (2013.01); *C12N 5/0605* (2013.01)

(58) Field of Classification Search
None
See application file for complete search history.

(56) References Cited

U.S. PATENT DOCUMENTS

2016/0090631 A1    3/2016    Stelling

FOREIGN PATENT DOCUMENTS

| CN | 101432441 | 5/2009 |
| CN | 101726585 | 6/2010 |
| CN | 103983794 | 8/2014 |
| CN | 108535228 | 9/2018 |
| CN | 109312332 | 2/2019 |
| CN | 111304153 | 6/2020 |
| CN | 111440696 | 7/2020 |
| CN | 112980779 | 6/2021 |

OTHER PUBLICATIONS

Li Dan et al., "Advances in the application of transcervical trophoblast cells in prenatal diagnosis", International Journal of Laboratory Medicine, submit with English abstract, Mar. 2019, pp. 597-600.
Fu Xiang-Long et al., "Progress on Isolation and Culture of Placental Trophoblast Cells in Vitro", Progress in Veterinary Medicine, submit with English abstract, Dec. 2012, pp. 97-100.
"International Search Report (Form PCT/ISA/210) of PCT/CN2022/081234," dated Jun. 20, 2022, with English translation thereof, pp. 1-6.

*Primary Examiner* — Teresa E Knight
(74) *Attorney, Agent, or Firm* — JCIPRNET

(57) ABSTRACT

The present invention discloses a method for isolating placental trophoblast cells from cervical exfoliated cells of a pregnant woman. Based on a specific antigen or combination expressed on the surface or inside of specific trophoblast cells, the designed microfluidic sorting chip or flow cytometer is used in the method to perform cell sorting of a cell suspension of a placental trophoblast sample, thus obtaining isolated and purified placental trophoblast cells. Compared with conventional methods, the method of the present invention has the advantages of non-invasively obtaining specimens and good specificity. Moreover, the method causes low risk of infection and abortion, allows earlier sampling time and can achieve the synchronous labeling of a plurality of antigens as well as identification and sorting of characteristic fluorescence signals; and the method has greatly improved accuracy and higher reliability and broader coverage area of detection results.

3 Claims, 14 Drawing Sheets

Cell mixture before sorting　　Positive cell result after sorting　　Negative cell result after sorting

METHOD FOR ISOLATING PLACENTAL TROPHOBLAST CELLS FROM CERVICAL EXFOLIATED CELLS OF PREGNANT WOMAN

CROSS-REFERENCE TO RELATED APPLICATION

This application is a 371 of international application of PCT application serial no. PCT/CN2022/081234, filed on Mar. 16, 2022, which claims the priority benefit of China application no. 202110549947.8, filed on May 20, 2021. The entirety of each of the above mentioned patent applications is hereby incorporated by reference herein and made a part of this specification.

TECHNICAL FIELD

The present invention belongs to the technical field of cell sorting. More specifically, the present invention relates to a method for isolating placental trophoblast cells from cervical exfoliated cells of a pregnant woman.

BACKGROUND

The three-level (pre-pregnancy, antenatal and newborn) prevention and control system is one of the important means to reduce birth defects and to improve population quality in China, among which prenatal screening and diagnosis is the most complex and most difficult part.

Currently, various disadvantages exist in clinically used prenatal diagnostic technologies such as, amniocentesis or cordocentesis, and non-invasive prenatal screening methods like fetal free nucleic acid sequencing. The amniocentesis and cordocentesis have high risks of infection during sampling and abortion, long analysis period, limited detection items and range. Moreover, the diagnosis time is limited within the middle and advanced stages of pregnancy, pregnant women have low acceptability of these two technologies, and the clinical treatment is difficult. The fetal free nucleic acid sequencing technology has extremely limited test range, and can only detect 3-5 designated chromosome aneuploid, and it's hard to avoid false positive and false negative cases using this method. Moreover, the technology has insufficient capacity in the detection of common mutations and the individual differences exist in the content of fetal free nucleic acids in maternal blood.

The applicant discloses a method for isolating trophoblast cells in patent application CN111304153A. In this method, by determining a specific antigen expressed on the surface of trophoblast cells and by using immunomagnetic beads carrying the corresponding specific antibody, the placental trophoblast cells are isolated from a cell suspension of a placental trophoblast sample and purified. Compared with the conventional amniocentesis and chorionic villus sampling, the technology has the advantages of non-invasive, earlier sampling time, low risk of infection and abortion, and similar reliability of test results. On the other hand, the technology still has space for the improvement of the applicable antibodies whose disclosed combinations are still limited, accuracy and specificity. The applicant team has carried out continuous research and development to the project.

SUMMARY

The objective of the present invention is to provide a method for isolating placental trophoblast cells from cervical exfoliated cells of a pregnant woman based on flow cytometry separation or microfluidics. The present invention not only overcomes the problems and defects of conventional methods, but also can achieve the synchronous labeling of a plurality of antigens as well as identification and sorting of characteristic fluorescence signals simultaneously; and the method has greatly improved accuracy and specificity superior to the previous immunomagnetic beads separation solution. Moreover, the method has advantages in the improvement of both cell quantity and quality. The number of cells obtained is larger than that of conventional methods, with good specificity and sensitivity.

The above objectives of the present invention are achieved by the following technical solutions:

a method for isolating trophoblast cells, including the following steps:

step (1) preparing a sample cell suspension from a sample of cervical exfoliated cell sap;

step (2) adding a specific antibody to the sample cell suspension for incubation;

the specific antibody is an antibody combination corresponding to the specific antigen(s) expressed on the surface of or inside of trophoblast cells; preferably, the specific antibody combination is HLA-G+CK7, HLA-G+CK18, HLA-G+β-HCG, CD31+HPL, MMP9+CD31, HLA-G+HPL, HLA-G+MMP9, HLA-G+CD31, HLA-G+P, CD31+P, HLA-G+CDH5, CD31+CDH5, CD31+CK7+HLA-G, HLA-G+CK18+CD31, HLA-G+β-HCG+CD31, CD31+HPL+HLA-G, MMP9+CD31+HLA-G, CD31+P+HLA-G or HLA-G+CDH5+CD31;

step (3) performing sorting of a cell resuspension incubated in the step (2) by a flow cytometer to obtain isolated and purified placental trophoblast cells;

alternatively, performing fluorescence labeling and microfluidics cell sorting of a cell resuspension incubated in the step (2) by a microfluidic sorting chip to obtain isolated and purified placental trophoblast cells.

Preferably, the microfluidic sorting chip in the step (3) has a structure: including a substrate and a cover plate fitted therewith; the chip is made via the injection molding technology from base material, including but not limited to acrylic.

One side of the substrate is provided with a main runner, a side runner A and a side runner B, and the two side runners are close to left and right end portions of the main runner, correspondingly.

Another side of the substrate is provided with an inlet C, an inlet S, an outlet N and an outlet T; all the two inlets and the two outlets penetrate the substrate to communicate with the runners on the other side; and a position of the inlet C corresponds to the left end portion of the main runner; a position of the inlet S corresponds to the end portion of the side runner A; a position of the outlet N corresponds to the right end portion of the main runner; and a position of the outlet T corresponds to the end portion of the side runner B.

A deflection electrode device is further disposed in the main runner and at a convergence site of the outlet N and the outlet T.

Preferably, the main runner, the side runner A and the side runner B have a width not greater than 1000 μm and a depth not greater than 500 μm.

More preferably, the main runner, the side runner A and the side runner B have a width of 500-1000 μm.

More preferably, the main runner, the side runner A and the side runner B have a width of 1000 μm.

In the microfluidic sorting chip, the inlet C is used for feeding the mixed cell sample to be sorted; the inlet S is used for feeding a buffer solution; the outlet T is used for collecting target cells, and the outlet N is used for collecting non-target cells.

During the sorting process, the mixed sample containing target cells flows into the main runner of the chip from the inlet C, and the buffer solution flows into the side runner from the inlet S; the two are mixed at the intersection of the runners and then continuously flow along the same direction of the main runner. When the mixed cells flow through the deflection electrode device, the runner into which the cells are about to flow is controlled by selected by controlling the on/off of the electrode; the target cells are sorted to reach the outlet T, while the non-target cells continue to flow along the main runner to reach the outlet N, thus completing the sorting.

Moreover, preferably, a primary antibody in the step (2) is incubated in the following conditions: reacting for 30-90 min at 4° C., preferably, reacting for 60 min at 4° C.; and a second antibody-fluorescent labeling complex is incubated in the following conditions: reacting for 20 min at 2° C.-8° C.

Preferably, the step (2) specifically includes: successively and specifically binding the primary antibody and the second antibody-fluorescent labeling complex to a target antigen step by step via incubation, wherein a washing and centrifugal separation technology is used to avoid cross contamination during the binding process.

Preferably, the step (3) specifically includes: feeding the incubated cell resuspension into the inlet C of the microfluidic sorting chip, feeding the buffer solution into the inlet S, then placing the microfluidic sorting chip in a cell sorter to carry out the sorting program, and collecting specimens at the outlet T at the end of the sorting program to obtain sorted trophoblast cells.

Preferably, a liquid-phase cell sorting system in the step (3) is 0.2%-0.4% Triton-X-100, preferably, 0.3% Triton-X-100. More preferably, PBS is used for preparation.

Preferably, the sorting conditions of the flow cytometer in the step (3) are as follows: a sample loading rate is adjusted within 1000-2000 events/s, and a collecting rate is 5.0.

Preferably, an optimal system of the cell suspension in the step (1) is 1×PBS containing 0.2%-0.4% FBS, preferably, 1×PBS containing 0.3% FBS.

Moreover, an application of the method in the construction of products for human STR authentication, human chromosome ploidy detection, thalassemia gene testing, epicophosis gene testing, whole exome sequencing, chromosome microdeletion/duplicate detection (a high-throughput sequencing method), or chromosome structure variation detection (a high-density chip method) shall also fall within the protection scope of the present invention.

The prevent invention has the following beneficial effects:

Compared with the conventional amniocentesis and chorion villus sampling, the method for isolating placental trophoblast cells based on flow cytometry separation or microfluidics provided by the present invention has the advantages of non-invasively obtaining specimens, earlier sampling time, low risk of infection and abortion, and the test result has higher reliability and broader coverage area. Whole genome nucleic acid samples of fetus can be obtained by such kind of specimen, which makes the detection and analysis of all the genetic diseases possible, and basically achieves the coverage of genetic diseases detection (chromosome ploidy, chromosome structure variation CNV, mitochondria, microdeletion/duplicate, single-gene mutation, SNP/STR genetic characteristics detection, and the like).

The method of the present invention can obtain considerable cells (thousands of cells, the designed minimum quality control standard is greater than 2000 positive cells), and can achieve the specimen detection by the conventional molecular assay technique without special operations. Moreover, the method of the present invention has no strict requirement for technicians and laboratory equipment, which reduces the technical thresholds and use costs and can be carried out in more medical institutions, capable of being popularized in wide range.

Meanwhile, the method provided by the present invention is a multi-labeling screening solution, which can achieve the synchronous labeling of a more plurality of antigens as well as identification and sorting of characteristic fluorescence signals simultaneously, and the accuracy has been greatly improved. Compared with the existing immunomagnetic beads and other technologies, the method of the present invention can both have the advantages of cell quantity and quality. The cells obtained are not only numerous, but also have minor injury, and the cells obtained have good quality, good detection specificity and sensitivity.

DETAILED DESCRIPTION OF EMBODIMENTS

The present invention will be further described in combination with the detailed embodiments of the description, and the embodiments are not used to limit the present invention in any form. Unless otherwise specified, the reagent, method and equipment used in the present invention are conventional reagent, method and equipment in the art.

Unless otherwise specified, the reagent and material used in the examples below are available on the market.

Example 1

Design of a Microfluidic Sorting Chip

Figure 1:
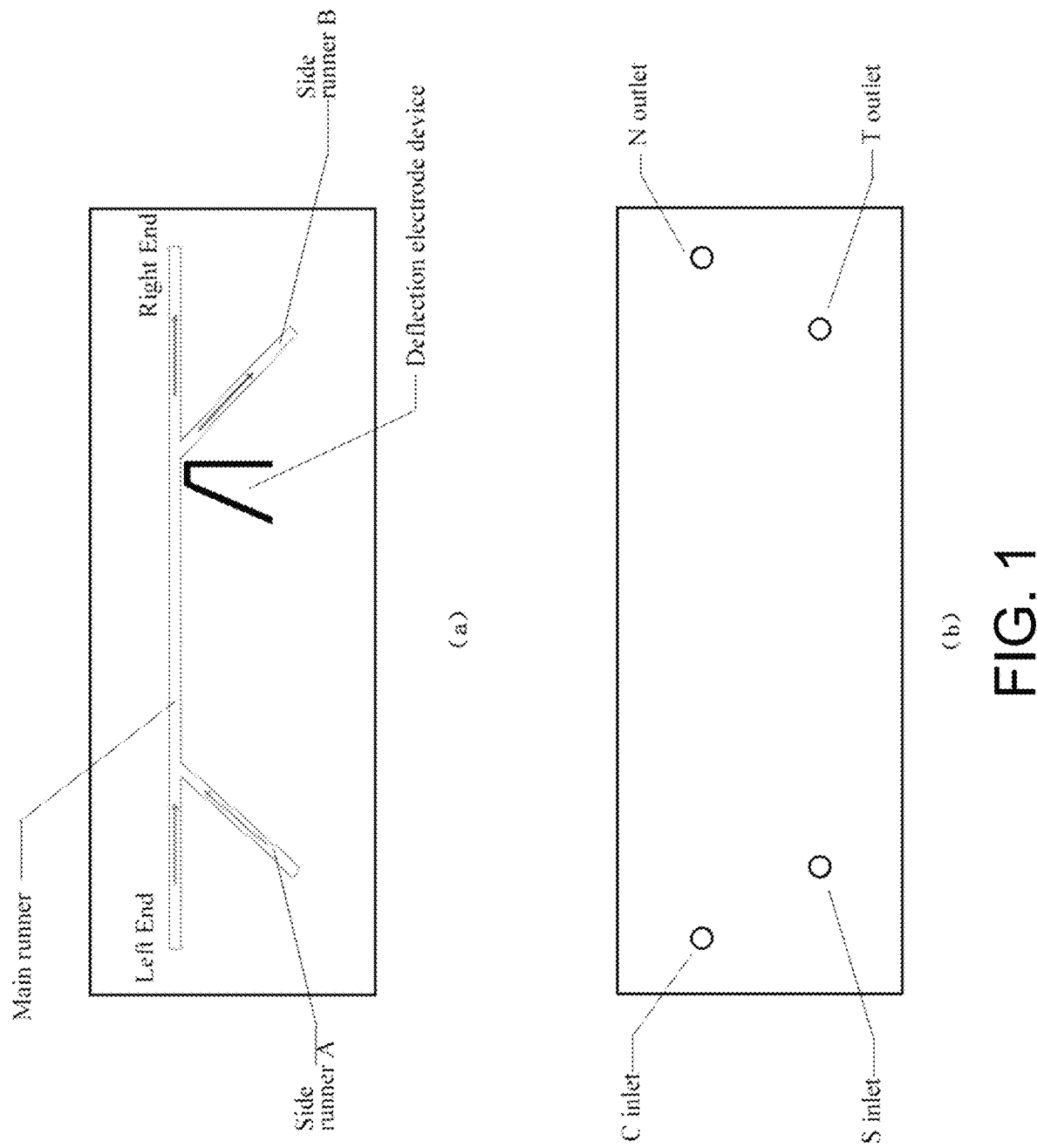
FIG. 1 is a schematic diagram showing a substrate structure of a microfluidic sorting chip; figures (a) and (b) respectively represent the two sides of the substrate.

The schematic diagram of the microfluidic sorting chip for isolating trophoblast cells from cervical exfoliated cells of a pregnant woman is shown in FIG. 1.

The structure of the microfluidic sorting chip is designed and described below: the chip is prepared by including but not limited to acrylic as a base material; a pipe shape of FIG. 1 was formed on one side of the base material via the injection molding technology, with the pipe width not greater than 1000 μm, and depth not greater than 500 μm, and another side of the base material is used for fitting to form a complete chip.

Specifically, the microfluidic sorting chip includes a substrate and a cover plate fitted therewith.

As shown in FIG. 1, one side of the substrate is provided with a main runner, a side runner A and a side runner B, and the two side runners are respectively close to left and right end portions of the main runner; and all the runners have a width of 1000 μm.

Another side of the substrate is provided with an inlet C (a liquid inlet for cell samples), an inlet S (a liquid inlet for buffer solution), an outlet N (a liquid storage hole for non-target cells) and an outlet T (a liquid storage hole for target cells); all the two inlets and the two outlets penetrate the substrate to communicate with the runners; and a position of the inlet C corresponds to the left end portion of the main runner; a position of the inlet S corresponds to the end portion of the side runner A; a position of the outlet N corresponds to the right end portion of the main runner; and a position of the outlet T corresponds to the end portion of the side runner B.

The inlet C is used for feeding the mixed cell samples to be sorted; the inlet S is used for feeding the buffer solution; the outlet T is used for collecting the target cells, and the outlet N is used for collecting the non-target cells.

Moreover, the main runner is further provided with a deflection electrode device for cell sorting; the deflection electrode device is specifically located at the intersection of the outlet N and the outlet T; the on/off of the electrode may be controlled according to the presence of a flow cell signal. Negatively-charged cells are subjected to deflection in the electromagnetic field formed by electrodes to flow into a designated pipe leading to the outlet N or the outlet T.

During the sorting process, the mixed sample containing target cells flows into the main runner of the chip from the inlet C, and the buffer solution flows into the side runner from the inlet S; the two are mixed at the intersection of the runners and then continuously flow along the same direction of the main runner. When the mixed cells flow through the deflection electrode device, the runner into which the cells flow are about to flow is selected by controlling the on/off of the electrode; the target cells are sorted to reach the outlet T, while the non-target cells continue to reach the outlet N along with the main runner, thus completing the sorting.

At the end of the sorting, the chip is immediately discarded, and a new chip needs to be exchanged before each sorting to ensure a clean, controllable and cross contamination-free sorting environment.

Example 2

Isolation of Trophoblast Cells from Cervical Exfoliated Cells of a Pregnant Woman Based on the Microfluidic Sorting Chip I. A Method for Isolating Trophoblast Cells Includes the Following Steps:

step 1, a sample cell suspension was prepared from a sample of cervical exfoliated cell sap; the specific method included the followings as shown in step (1)-step (5);

step 2, a specific antibody was added to the sample cell suspension for incubation; and the specific method included the followings as shown in step (6)-step (14);

step 3, fluorescence labeling and microfluidics cell sorting was performed on a cell resuspension incubated in the step 2 by the microfluidic sorting chip in Example 1; the specific method included the followings as shown in step (15)-step (18).

The combinations of specific antibodies are shown in Table 1:

TABLE 1

Combinations of antigens and antibodies expressed on the trophoblast cells

| Antibody combinations | HLA-G + CK7, HLA-G + CK18, HLA-G + β-HCG, CD31 + HPL, MMP9 + CD31, HLA-G + HPL, HLA-G + MMP9, HLA-G + CD31, HLA-G + P, CD31 + P, HLA-G + CDH5, CD31 + CDH5, CD31 + CK7 + HLA-G, HLA-G + CKI8 + CD31, HLA-G + β-HCG + CD31, CD31 + HPL + HLA-G, MMP9 + CD31 + HLA-G, CD31 + P + HLA-G, HLA-G + CDH5 + CD31 |

The information of the corresponding antigens is shown below:

| Specific antigens on the surface of trophoblast cells | Corresponding receptors | Available monoclonal antibodies |
| --- | --- | --- |
| HLA-G (human leucocyte antigen G) | LIR1/ILT2, LIR2/ILT4, p49/KIR2DL4, BY55 | 4H84 (BD Biosciences) |
| β-HCG (human chorionic gonadotropin) | LH/HCG receptor | 5H4-E2 (Thermo Scientific) |
| Cytokeratin7 (CK-7) | | OV-TL 12/30 (DAKO), mouse-anti-human cytokeratin 7 (CK-7) monoclonal antibody |
| Cytokeratin18 (CK-18) | | mouse-anti-human CK18 monoclonal antibody (ab181597) (Abcam company) |
| Matrix metalloproteinase 9 (MMP9) | Type-IV, V, VII and X collagens, gelatins and elastic fibers | 4H3 (R & D Systems) |
| VE-Cadherin (CDH5) | | 2158 (Cell Signaling Technology) |
| Platelet endothelial cell adhesion molecule precursor PECAM1 (CD31) | | 89C2 (Cell Signaling Technology) |

TABLE 1-continued

Combinations of antigens and
antibodies expressed on the trophoblast cells

| | |
|---|---|
| Human placental lactogen (HPL) | Prolactin receptor |
| Progesterone (P) | Progesterone receptor (PGR) |

II. Specifically, the Sorting Method of the Trophoblast Cells Includes the Following Steps of:

step (1), a cell preserving solution (containing the cervical exfoliated cells) was mixed on an oscillating mixer evenly for 5 min;

step (2), the preserving solution was transferred into a 15 mL centrifugal tube, and 3 mL 1×PBS was added to the bottle of the preserving solution, and mixed evenly by oscillation, then the solution was transferred into the same 15 mL centrifugal tube;

step (3), the solution was centrifuged for 10 min at 3000 rpm, and supernatant was discarded;

step (4), 1 mL 1×PBST was added and mixed well and transferred to a 1.5 mL EP tube, and centrifuged for 5 min at 3000 rpm, and supernatant was discarded;

step (5), the step (4) was repeated twice to prepare a cell suspension;

step (6), 200 μL 0.3% Triton X-100 was added and mixed well, then permeabilizd at room temperature for 20 min;

step (7), the step (4) was repeated for three times;

step (8), addition of a primary antibody: 200 μL of mouse-anti-human CK7 monoclonal antibody, mouse-anti-human CK18 monoclonal antibody, mouse-anti-human β-HCG monoclonal antibody, mouse-anti-human MMP9 monoclonal antibody, mouse-anti-human CDH5 monoclonal antibody, mouse-anti-human P monoclonal antibody, mouse-anti-human hPL monoclonal antibody, rabbit-anti-human HLA-G monoclonal antibody, and rabbit-anti-human CD31 monoclonal antibody (Abeam company) which were diluted by proportions were respectively added, and mixed well, incubating for 60 min at 4° C.;

step (9), the step (4) was repeated for three times;

step (10), addition of a secondary antibody-fluorescent labeling complex: 200 μL of goat-anti-rabbit and goat-anti-mouse antibodies which were diluted by proportions were mixed well, incubating for 60 min at 37° C.;

step (11), the step (4) was repeated for three times, and 200 μL buffer (DPBS+0.1% BSA+2 mM EDTA) was used for resuspending;

step (12), reaction was performed for 20 min at 2° C.-8° C.;

step (13), 1 mL 1×PBST was added and mixed well and transferred to a 1.5 mL EP tube, and centrifuged for 5 min at 3000 rpm and supernatant was discarded;

step (14), the step (13) was repeated for two to three times, and 200 μL 1×PBST was added for resuspending to obtain a cell resuspension;

step (15), the obtained cell resuspension was fed into the inlet C of the microfluidic sorting chip in Example 1, and 1×PBST was fed into the inlet S;

step (16), the microfluidic sorting chip was placed and fixed on an objective table of a cell sorter, and the cell sorter was turned on to set the designated program for operation;

step (17), at the end of the program, specimens at the outlet T were collected to obtain the sorted trophoblast cells;

step (18), specimens at the outlet N were collected to obtain the remaining cells obtained after trophoblast cells were removed from the cervical exfoliated cells.

Example 3

Method for Isolating Trophoblast Cells from Cervical Exfoliated Cells of a Pregnant Woman Based on a Flow Cytometer A Method for Sorting Trophoblast Cells Includes the Following Steps:

step 1, a sample cell suspension was prepared from a sample of cervical exfoliated cell sap; and the specific method was the same as those in step (1)-step (5) of Example 2;

step 2, a specific antibody was added to the sample cell suspension for incubation; and the specific method was the same as those in step (6)-step (14) of Example 2; combinations of the specific antibodies are the same as those in the Table 1 above;

step 3, a cell resuspension incubated in step 2 was subjected to fluorescence labeling and sorting by a flow cytometer (BDFACSAria type II, USA), including the following steps:

step 1), the flow cytometer was turned on for daily startup operation according to the instructions;

step 2), the instrument was subjected to liquid flow adjustment such that the breakpoint position of the liquid flow was located in the middle-upper part of the window;

step 3), sorting liquid path was adjusted to confirm the delay of liquid drops, and a sample loading rate was adjusted within 1000-2000 events/s;

step 4), 5 mL flow tubes were chosen as collection devices; the number of the sorted cells was 3000, and direction was left, and cell population to be sorted was added, and subjected to gating successively, and then loaded the collecting tubes;

step 5), the incubated cell suspension was put into a sample warehouse, and a collecting rate was set 5.0 and sample loading was performed;

step 6), voltage was adjusted within the scope of 300-500 V such that the compensation between fluorescent dyes was kept as small as possible; the gate position was adjusted such that positive cells were located in the center, and cells within the gate were collected; and the cells in the collecting tube were namely, the selected target cells.

Figure 2:
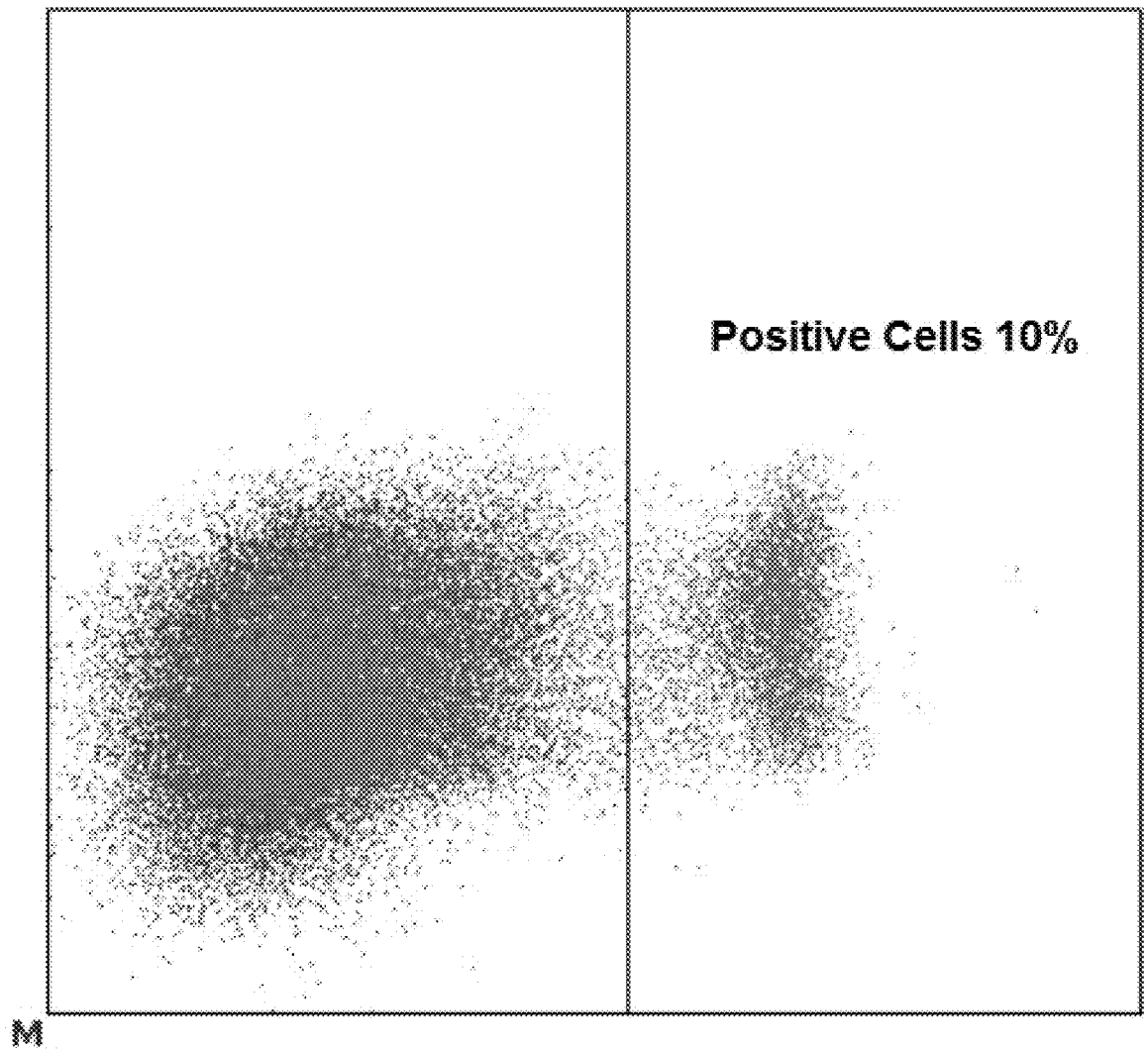
FIG. 2 shows a mono-fluorescence labeled positive cell population selected in flow cytometry sorting.
Figure 3:
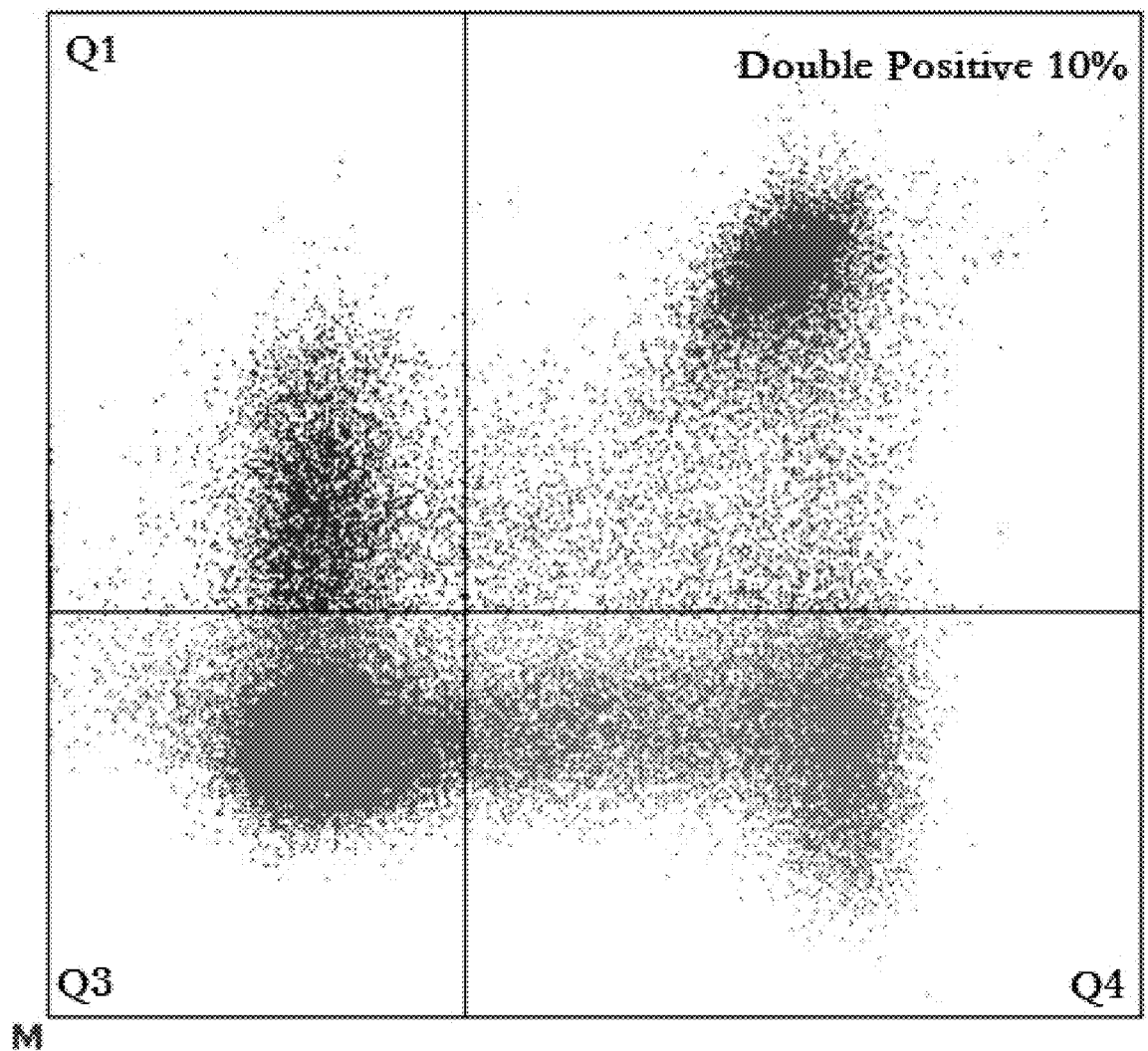
FIG. 3 shows a bifluorescence labeled positive cell population selected in flow cytometry sorting.
Figure 4:
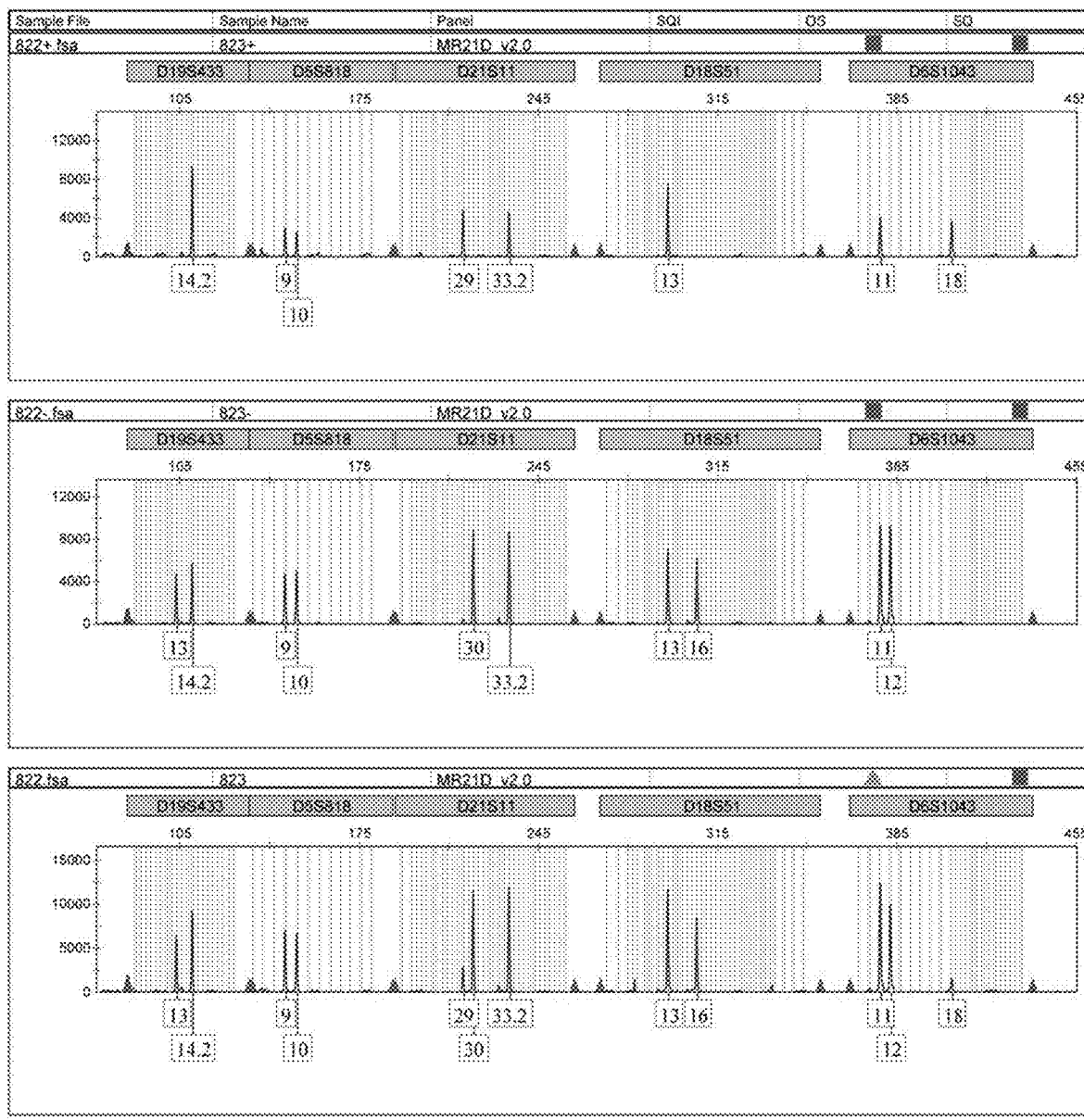
FIG. 4 is an FAM-labeled channel 1; "822−" represents the rest specimens after sorting; "822+" represents sorted specimens; "822" represents specimens before sorting.
Figure 5:
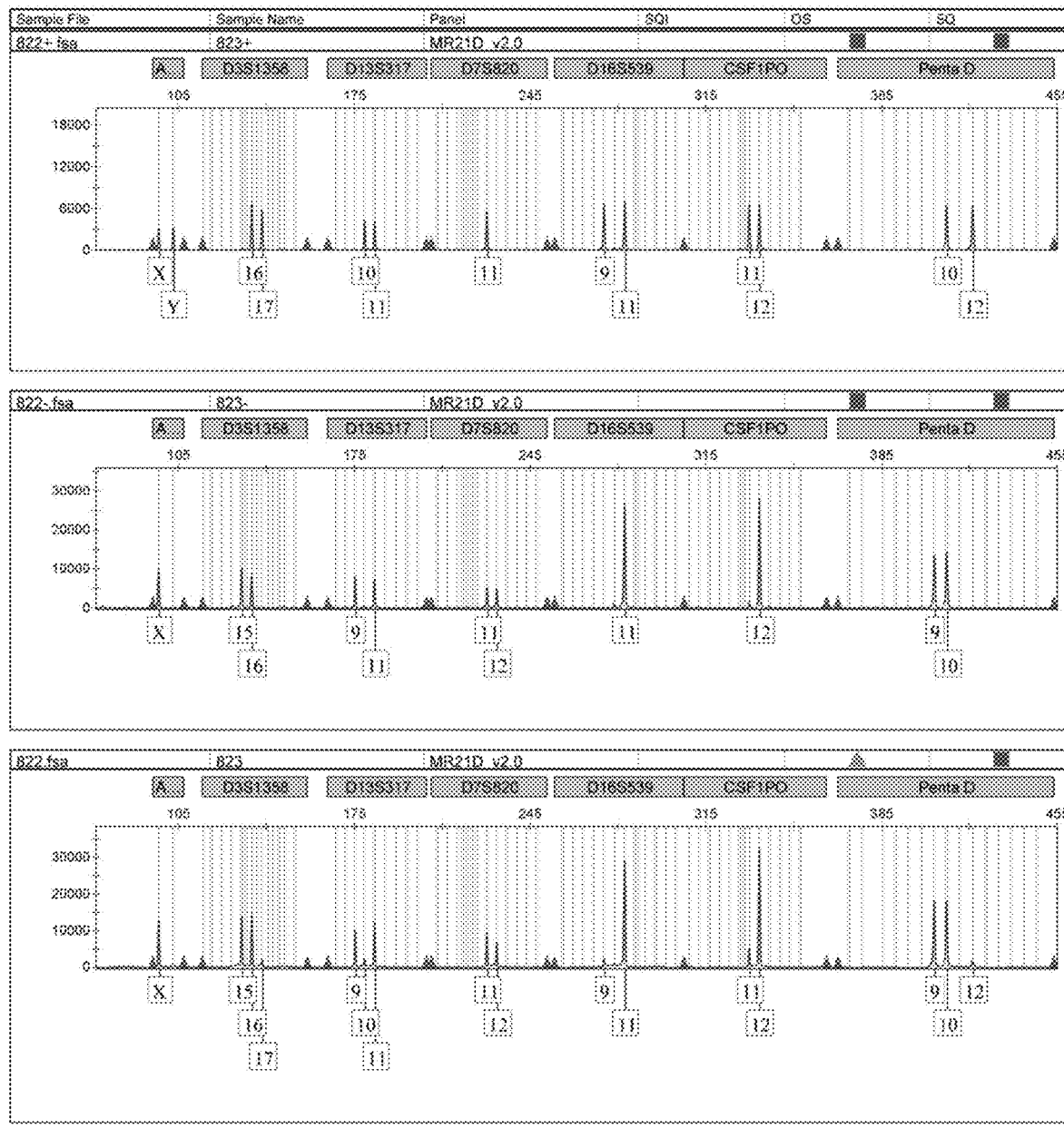
FIG. 5 is an HEX-labeled channel 2.
Figure 6:
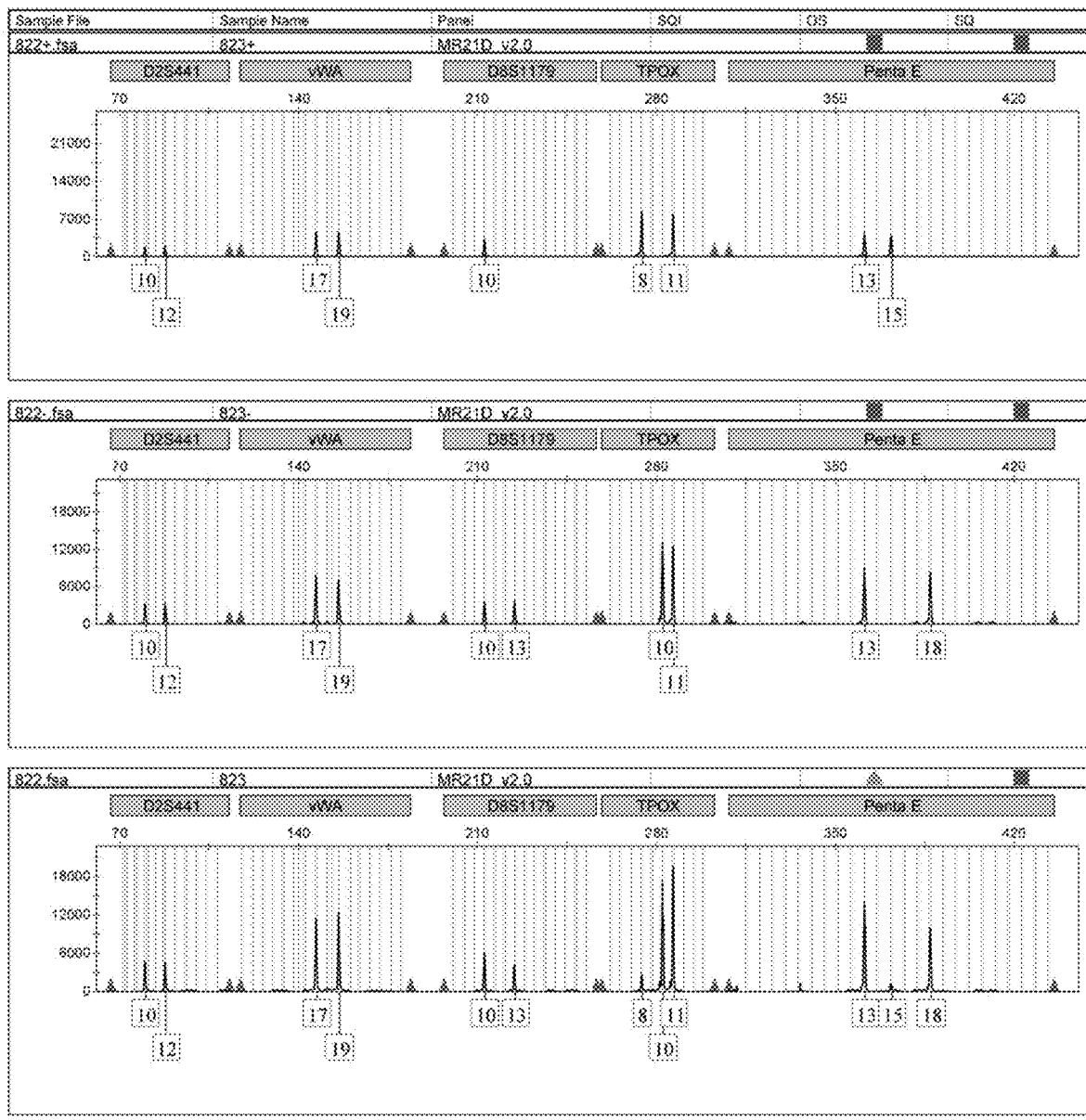
FIG. 6 is a TAMRA-labeled channel 3.
Figure 7:
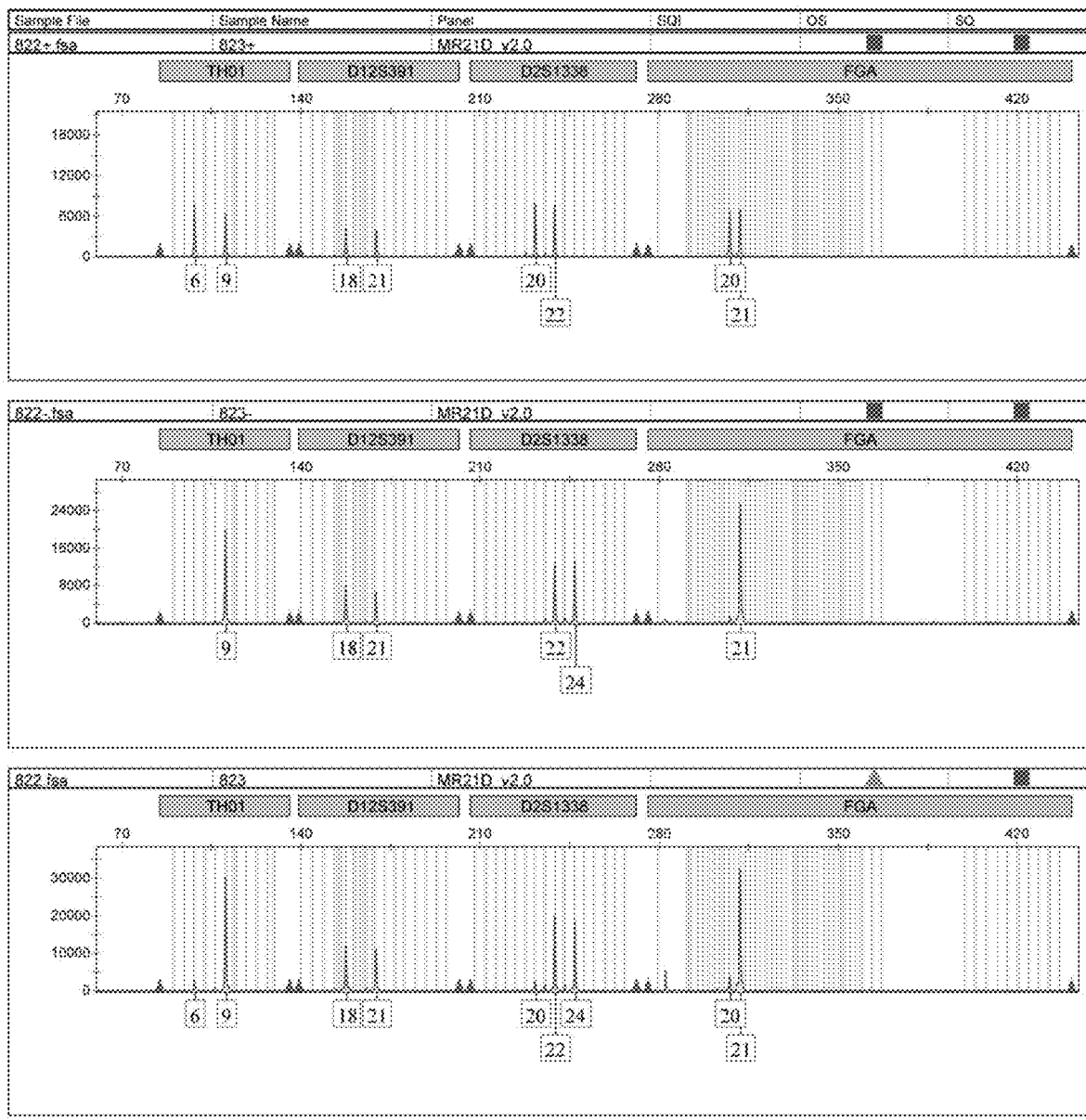
FIG. 7 is a ROX-labeled channel 4.

The target cell population was obtained according to the given labeling combinations, as shown in FIGS. 2-3. FIG. 2 shows a sorting result of mono-fluorescence labeling, and FIG. 3 shows a sorting result of bifluorescence labeling.

Example 4

Application Case of the Method—Human STR Authentication

1. Trophoblast cells were sorted and isolated from a sample (cervical exfoliated cells) according to the method of the above Example 2.

2. The isolated trophoblast cells and cervical exfoliated cells of a pregnant woman were subjected to DNA extraction:
1) the sorted trophoblast cells (the trophoblast cells obtained in the step (17) of the cell sorting method in Example 2), and the cells obtained in the step (18) of the cell sorting method in Example 2 (the remaining cells obtained after trophoblast cells were removed from the cervical exfoliated cells) were respectively centrifuged for 3 min at 12000 rpm;
2) supernatant was discarded, and 200 µL solution P was added for resuspending precipitates;
3) 20 µL protease K and 200 µL solution L were added and mixed well;
4) the mixed solution was treated in a warm bath at 56° C. for 20 min and overturned and mixed well;
5) 200 µL absolute ethyl alcohol was added and mixed well, and then, the mixed solution was transferred to an adsorption column, and centrifuged at 10000 rpm for 1 min, then waste solution in the collecting tube was discarded;
6) 500 µL W1 was added and centrifuged at 10000 rpm for 1 min, then waste solution in the collecting tube was discarded;
7) 500 µL W2 was added and centrifuged at 10000 rpm for 1 min, then waste solution in the collecting tube was discarded;
8) 500 µL W2 was added and centrifuged at 10000 rpm for 1 min, then waste solution in the collecting tube was discarded;
9) the blank tube was centrifuged at 12000 rpm for 3 min, then the collecting tube was discarded;
10) the adsorption column was put into a new 1.5 mL centrifugal tube, uncovered and standing for 2 min, then 50 µL TE was added and centrifuged at 12000 rpm for 2 min after standing for 5 min, and the adsorption column was discarded;
11) the extracted DNA concentration and purity were determined.
3. The isolated trophoblast cells and cervical exfoliated cells of a pregnant woman were subjected to DNA extraction, and then subjected to PCR amplification with Microread D-21 human STR authentication kit; the PCR products were subjected to capillary electrophoresis with a 3500xL sequencer, and the instrument was subjected to fluorescent calibration with G5-Matrix Standard, and corresponding Panels and bins files were compiled, and software GeneMapper ID version 3.0 was used for result analysis.
4. STR Detection
1) PCR amplification, and the amplification system is shown in Table 2:

TABLE 2

| PCR amplification system | |
| --- | --- |
| Reagent | Volume (µL) |
| 2.5× Buffer D | 10 |
| 5× Primer MIX | 5 |
| Polymerase MIX 1 | 0.55 |
| DNA | 1 |
| H₂O | Up to 25 |

Figure 8:
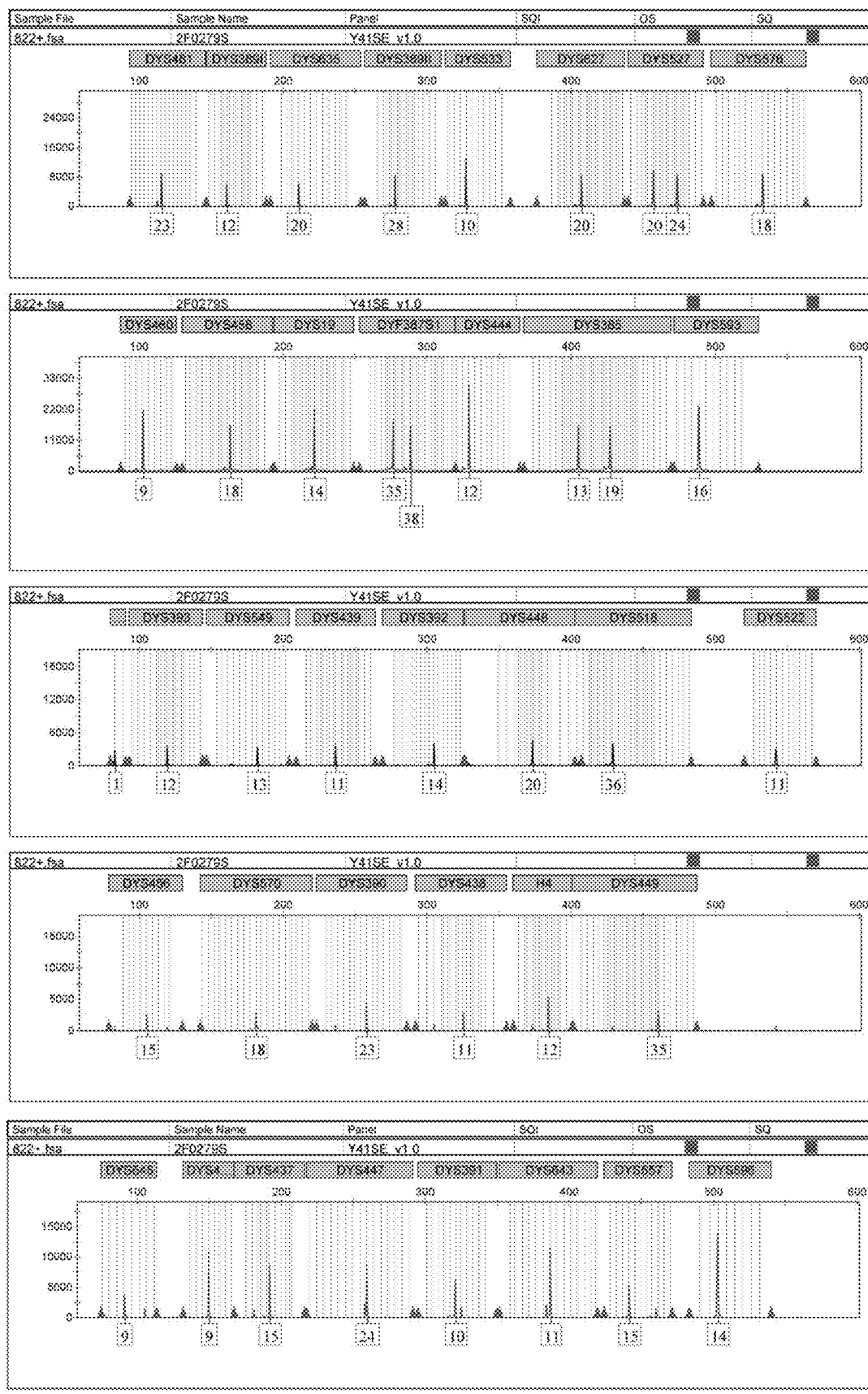
FIG. 8 is a schematic diagram showing a test result of Y-STR of the Y-chromosome containing specimen in the sorted plasmoditrophoblast cells.

PCR reaction procedure: PCR reaction was performed for 10 min at 50° C. and for 4 min at 96° C. (5 sec at 94° C. and 1 min+10 sec at 60° C.)×27 cycles, for 30 min at 60° C., and preserved at 15° C.
2) STR test result
8.7 µL Hidi and 0.3 µL internal reference were mixed well according to the instructions, and added with 1 mL amplified product, then the treated PCR product was subjected to capillary electrophoresis with a 3500xL sequencer, and the instrument was subjected to fluorescent calibration with GS-Matrix Standard, and corresponding Panels and bins files were compiled, and software GeneMapper ID version 3.0 was used for result analysis. Results are shown in FIGS. 4-7. The results show that besides the DNA of the pregnant woman, there was exactly another individual DNA information, and the DNA information has a strong genetic relationship with the pregnant woman.
3) Y-STR detection
The specimen of Y chromosome detected in STR was subjected to Y-STR detection with a Microread 40Y kit. Results are shown in FIG. 8, and the results show that there exists male DNA in the specimen.

Example 5

Application Case of the Method—Detection of Epicophosis-Susceptible Genes

Cervical exfoliated cells of a pregnant woman (sample source: Guangzhou Hybribio Medical Laboratory) were subjected to epicophosis-susceptible gene testing with a commercial kit (an epicophosis-susceptible gene kit (PCR+ flow-through hybridization), Chaozhou Hybribio Biochemistry Co., Ltd., Registration Certificate No. for Medical Device of the People's Republic of China: 20153401698) according to the method of Example 2; specifically, 9 mutation sites (mtDNA1494, mtDNA1555, SLC26A4-IVS7 (-2), SLC26A4-2168, GJB2-35, GJB2-176, GJB2-235, GJB2-299 and GJB3-538) of the epicophosis-related genes (GJB2, GJB3, SLC26A4 and mtDNA) were subjected to testing.

Figure 9:
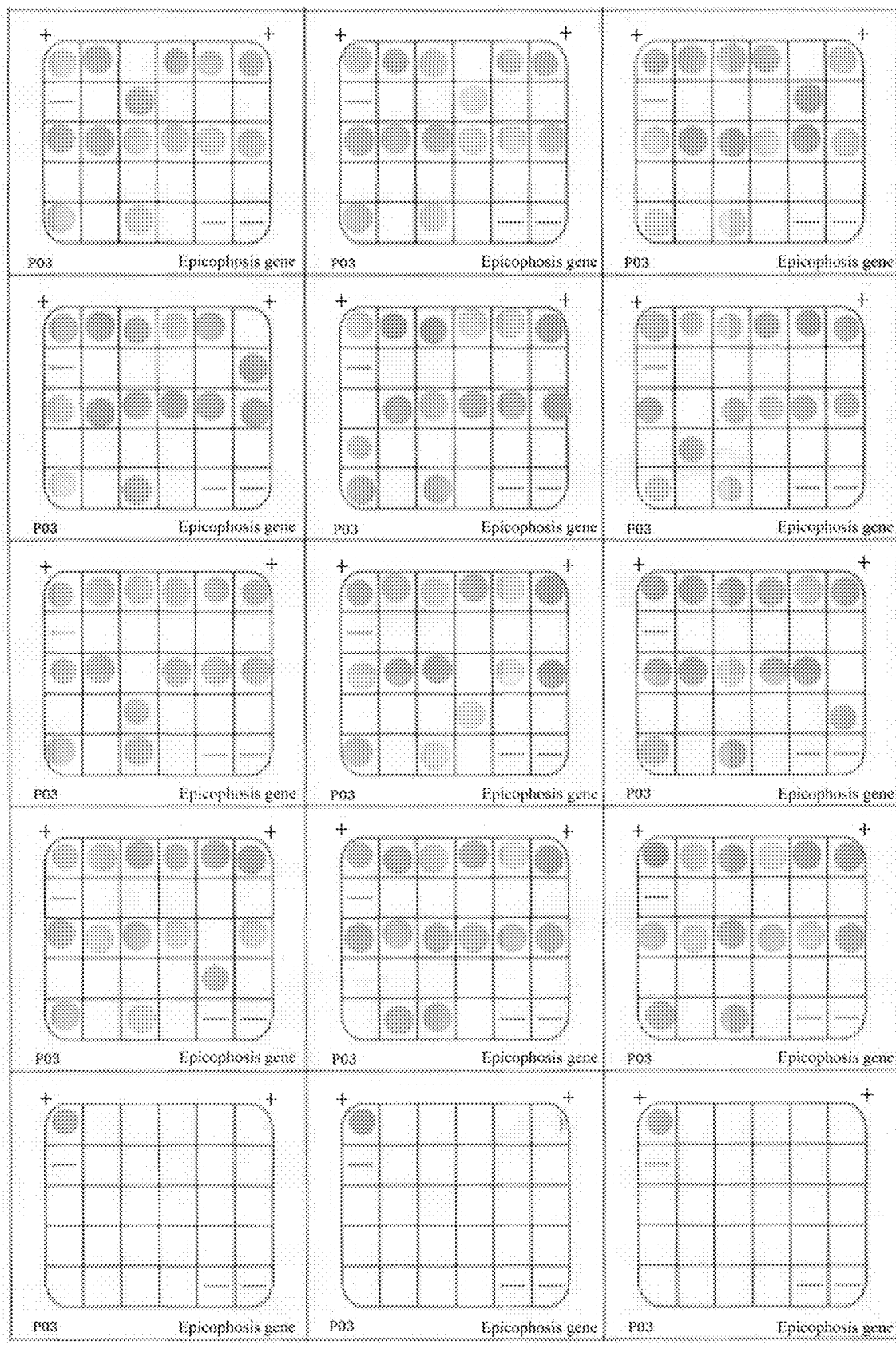
FIG. 9 is a test result of epicophosis genes of the sorted specimen.

The DNA extraction method of the cervical exfoliated cells of a pregnant woman in Example 4 was used, and then a commercial kit (epicophosis-susceptible gene kit (PCR+ flow-through hybridization), Chaozhou Hybribio Biochemistry Co., Ltd., Registration Certificate No. for Medical Device of the People's Republic of China: 20153401698) was used for subsequent testing. Specific operations are specifically shown in the instructions. Raw data are shown in FIG. 9; and result analysis are shown in Table 3.

TABLE 3

| Epicophosis result analysis | | |
| --- | --- | --- |
| 155M homozygosity | 176M homozygosity | 235M homozygosity |
| 299M homozygosity | 1494M homozygosity | 1555M homozygosity |
| 7445M homozygosity | 538M homozygosity | 2168M homozygosity |
| IVS-M homozygosity | 1229M homozygosity | Normal sample |
| Blank control | Blank control | Blank control |

The results indicate that the test results are consistent with the clinical test results.

Example 6

Application Case of the Method—Detection of Thalassemia-Related Genes

Cervical exfoliated cells of a pregnant woman (sample source: remaining nucleic acid samples of the humanized specimen detected by Hybribio Medical Laboratory) were subjected to epicophosis-susceptible gene testing with a commercial kit (α- and β-thalassemia gene kit (PCR+membrane hybridization method), Chaozhou Hybribio Biochemistry Co., Ltd., SFDA Certified No.: 3400399, 2012) according to the method of Example 2; specifically, 3 common α-thalassemia deletion types ($-^{SEA}$, $-α^{3.7}$, $-α^{4.2}$), 2 α-thalassemia mutant types (CS and QS) and 11 β-thalassemia mutant types (CD14-15, CD17, CD27-28, CD41-42, CD43, CD71-72, -28, -29, IVS-I-1, IVS-II-654 and β EN) were subjected to testing.

Figure 10:
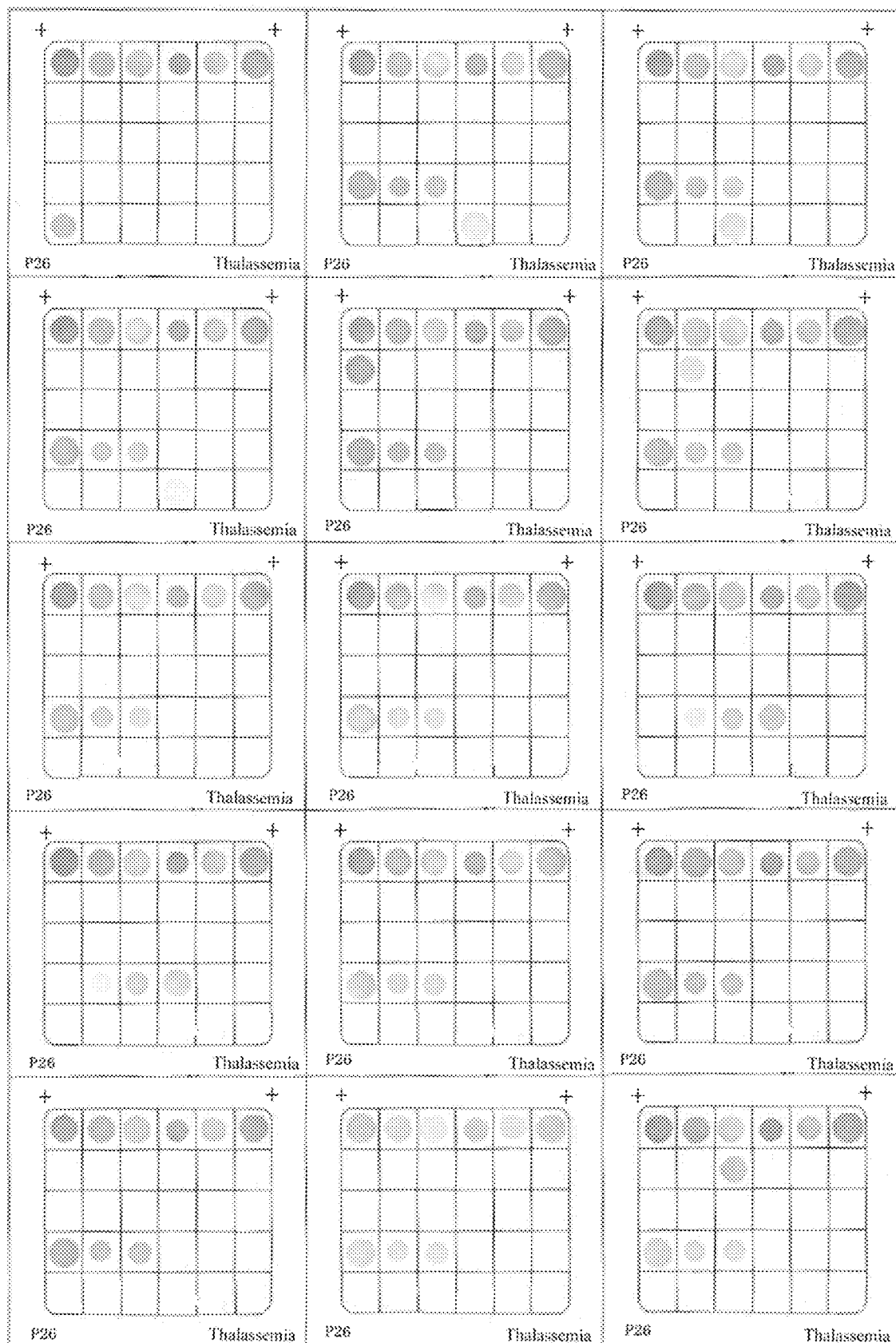
FIG. 10 is a test result of thalassemia genes of the sorted specimen.

The DNA extraction method of the cervical exfoliated cells of a pregnant woman in Example 4 was used, and then a commercial kit (α- and β-thalassemia gene kit (PCR+membrane hybridization method), Chaozhou Hybribio Biochemistry Co., Ltd., SFDA Certified No.: 3400399, 2012) was used for subsequent testing. Specific operations are specifically shown in the instructions. Raw data are shown in FIG. 10; and result analysis is shown in Table 4.

TABLE 4

Thalassemia result analysis

| Southeast Asia deletion (--SEA/--SEA) | Left deletion (-α4.2/αα) | QS mutation heterozygote |
|---|---|---|
| Left deletion (-α4.2/αα) | 41-42M heterozygote | 17M heterozygote |
| Normal sample | Normal sample | Right deletion (-α3.7/-α3.7) |
| Right deletion (-α3.7/-α3.7) | Normal sample | Left deletion (-α4.2/αα) |
| Normal sample | Normal sample | 654M heterozygote |

The results indicate that the test results are consistent with the clinical test results.

Example 7

Application Case of the Method—Whole Exome Sequencing

1. Cervical exfoliated cell specimen and amniotic fluid specimen of a pregnant woman were obtained in a known epicophosis family (father, mother (16-week pregnancy), eldest child (deaf son) and youngest son (deaf son)) according to the method in Example 2. The pregnant woman and other family members were subjected to whole blood specimen collection and DNA extraction (after the cervical exfoliated cells of the pregnant woman were sorted, the specimen was obtained by the extraction method of Example 4; the amniotic fluid and the whole blood specimens were extracted by a human whole blood genome DNA extraction kit (Hybribio, China) (sample source: a humanized specimen detected by Hybribio Medical Laboratory)); and the obtained human genome DNA was subjected to whole exome sequencing (WES) with a whole exome kit (iGeneTech Biotechnology (Beijing) Co., Ltd., Art. No.: T086V4):

The genome DNA was processed into 300 bp fragments with a transposase Tn5 to construct a DNA library; adapters P5, P7, index1, 2 were added at both terminals; a proper length of DNA fragments was chosen, amplified and purified, then hybridized with the exon probe library with biotin; strong binding force of the biotin to streptavidin was used to bind streptavidin-carrying magnetic beads with the probe which had been bound to the target library; the magnetic beads were adsorbed and supernatant was removed, and DNA on the magnetic beads was eluted, and the library was subjected to PCR amplification, and quality evaluation; and sequencing on a machine was performed.

2. Whole exome sequencing result

Figure 11:
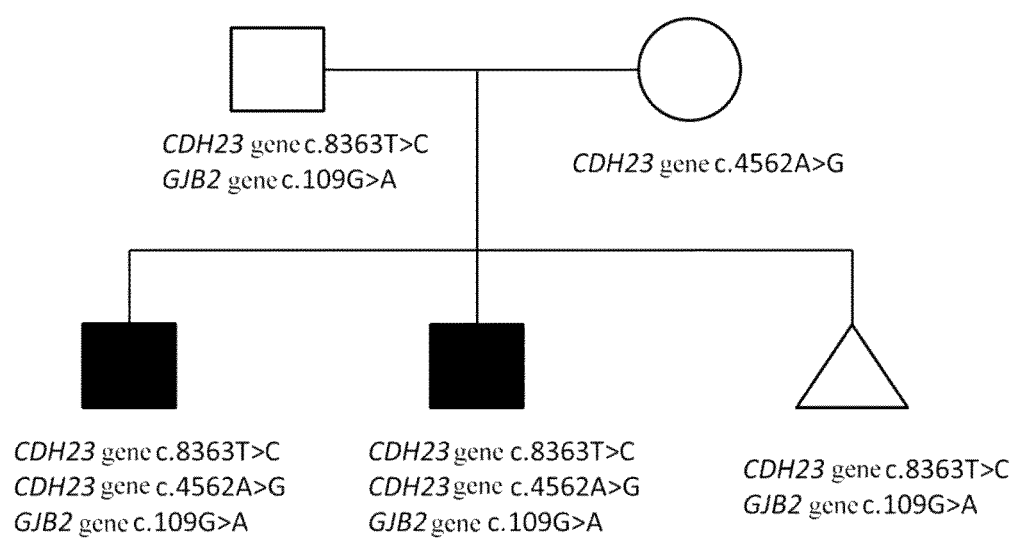
FIG. 11 shows a family genogram carrying detected family pathogenic mutations.

Whole exome sequencing was performed with a high-throughput sequencing technology, and the detected pathogenic or suspected pathogenic site was verified with Sanger sequencing. The test sample was an amniotic fluid specimen (16-week pregnancy); two brothers were deaf and parents were normal. CDH23 gene c.8363T>C (p.Leu2788Pro) heterozygous mutation and GJB2 gene c.109G>A (p.Val127Ile) heterozygous mutation were detected in the sample. Family genogram is shown in FIG. 11.

The results indicate that pathogenic mutation was effectively detected from the sorted exfoliated cell specimen, which is completely consistent with the amniotic fluid specimen.

Pathogenesis and pathogenic mutation-carrying situations can be found from the test results.

Example 8

Application Case of the Method—Detection of Whole Genome DNA Copy Number Variation (CNV)

1. The whole genome DNA copy number variation was detected with a CytoOneArray chromosome chip and a supporting kit from Phalanx Biotech according to the theory (aCGH) of comparative genomic hybridization: the sorted trophoblast cells by the method of Example 2 were extracted by the DNA extraction method of the cervical exfoliated cells of the pregnant woman in Example 4; the obtained human genome DNA was subjected to fragmentation, amplification pretreatment, amplification and PCR product purification, then labeled by two different fluorescent dyes (normal sample was labeled by Cy3, showing green, and the patient sample was labeled by Cy5, showing red); the fluorescent product was poured into the chip after being purified, and the chip was washed and scanned to obtain results.

2. Test results of the whole genome DNA copy number variation (CNV)

Figure 12:
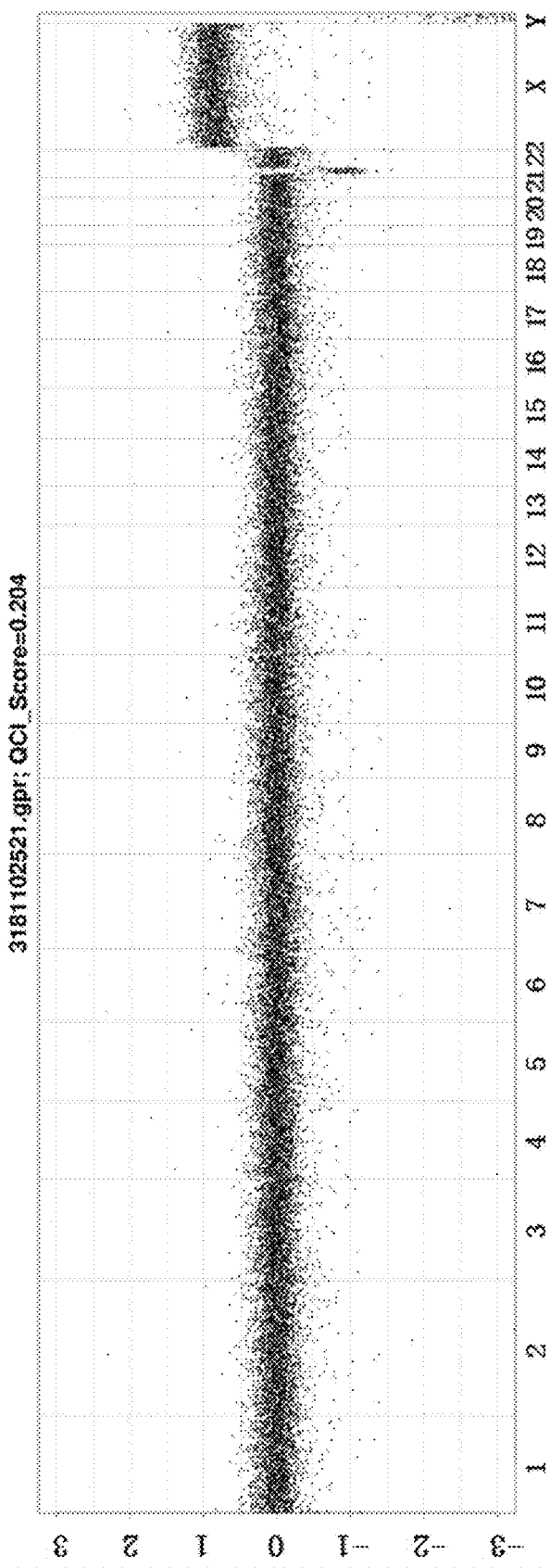
FIG. 12 is a schematic diagram showing whole chromosomes.
Figure 13:
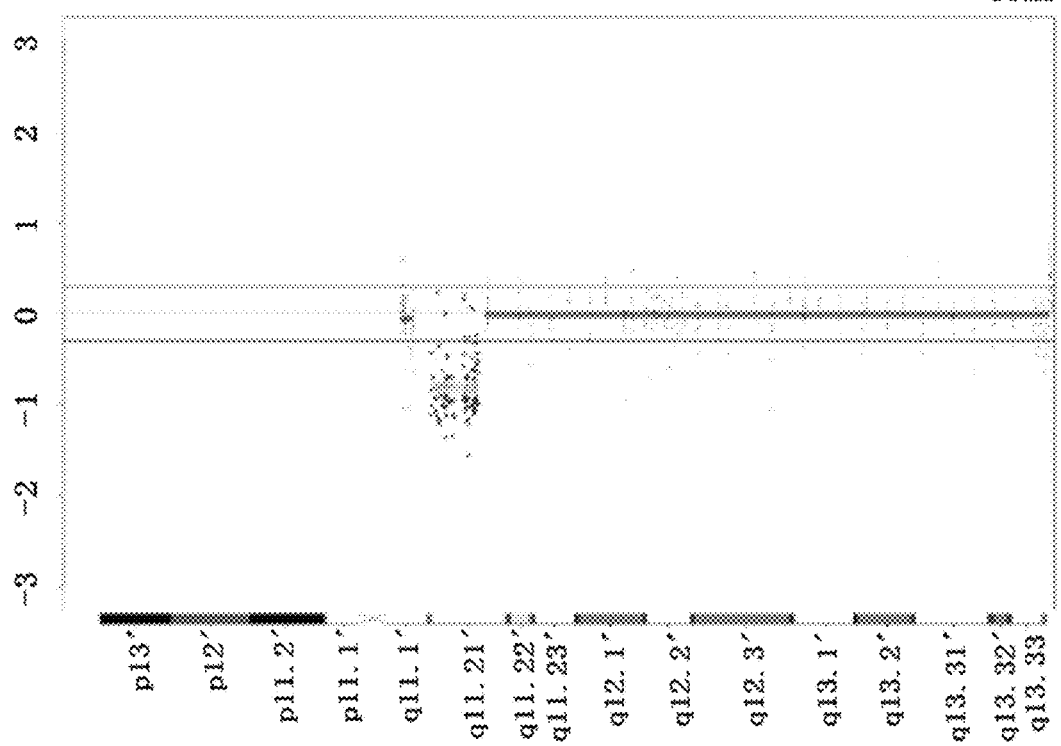
FIG. 13 is a schematic diagram showing abnormal chromosomes.

The schematic diagram of whole chromosomes is shown in FIG. 12 and the schematic diagram of abnormal chromosomes is shown in FIG. 13. In FIG. 13, the horizontal axis represents the schematic diagram of a chromosome zone, and longitudinal axis shows a signal ratio of the sample to the standard sample (represented by a log 2 ratio). When the chromosome CNV has a significant difference, it is represented by different colors. The region (Gain) where chromosome is amplified is represented by blue, and the region (Loss) where chromosome is deleted is represented by red. The length and value of the black line respectively represent the mean size and signal of each Segment.

One abnormity is detected in the sample, namely, 22q11.21 deletion; the start-end positions [UCSC hg19] of the abnormal fragment are arr22q11.21 (19006943_21461068)×1 with a size of 2.454 Mb. Related disease area is Pathogenic (pathogenicity, ACMG classification); and such abnormal fragment covers 106 ISCA genes, such as TBX1, CRKL, GP1BB, SLC25A1, DGCR10, TSSK1A, GSC2 and CLTCL1. The regional anomaly is located at 22q11.2 recurrent (DGS/VCFS) region (includes TBX1). The deletion of 22q11.2 proximal (A-D) region is related to the DiGeorge/Velocardiofacial (DGS/VCFS) syndrome which is generally clinically featured by congenital heart disease, heart abnormity, characteristic facial features, DD/ID, behavior disorders, immune deficiency and hypocalcemia (PMID 25217958). The regional anomaly is located at 22q11.2 recurrent region (central, B/C-D) (includes CRKL). The clinical phenotypes possibly caused by the region deletion includes: deformed facial features, growth restriction/short stature, central nervous system abnormity/attack, developmental retardation, dysgnosia, skeletal anomalies, cardiovascular defects, urogenital system anomalies, immune deficiency/repeated infection (PMID 25123976).

The results indicate that the sorted cell specimen can be effectively subjected to chromosome structure variation detection and corresponding mutations can be detected.

Example 9

Figure 14:
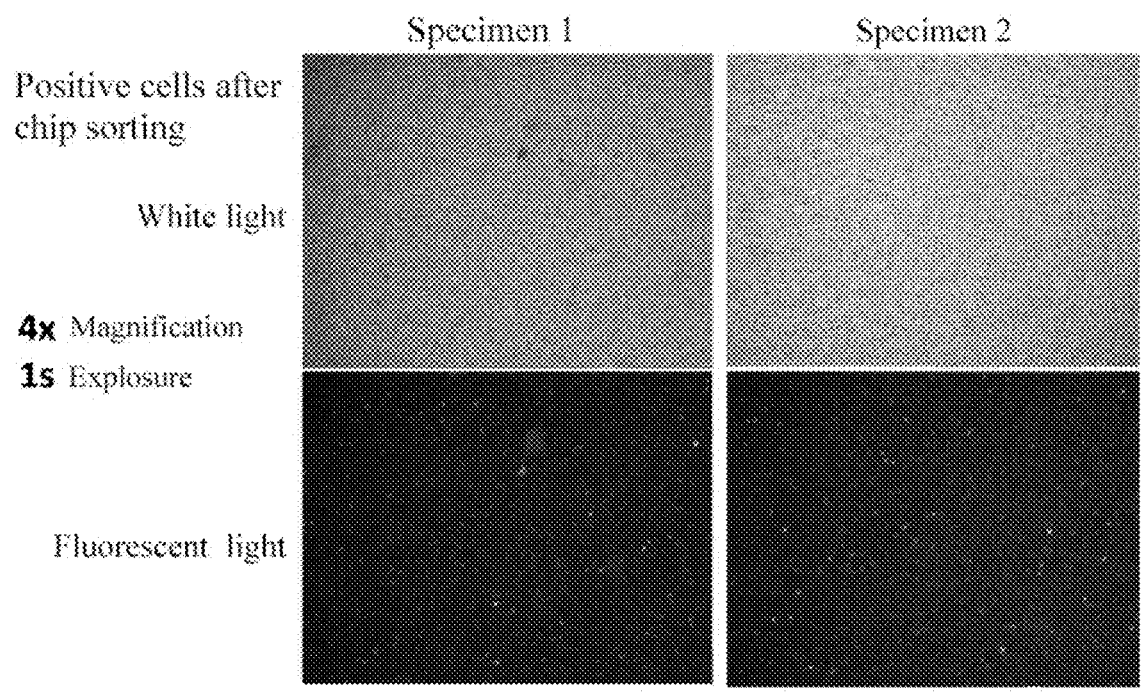
FIG. 14 is a picture showing positive cells sorted by the method of the present invention.
Figure 15:
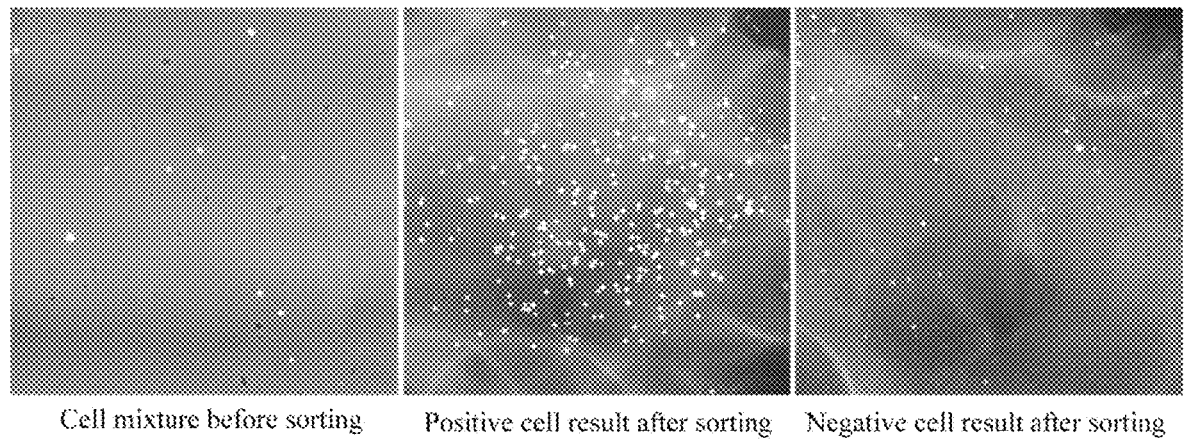
FIG. 15 is a picture showing comparison of positive cells and negative cells before and after sorting using the method of the present invention.
Figure 16:
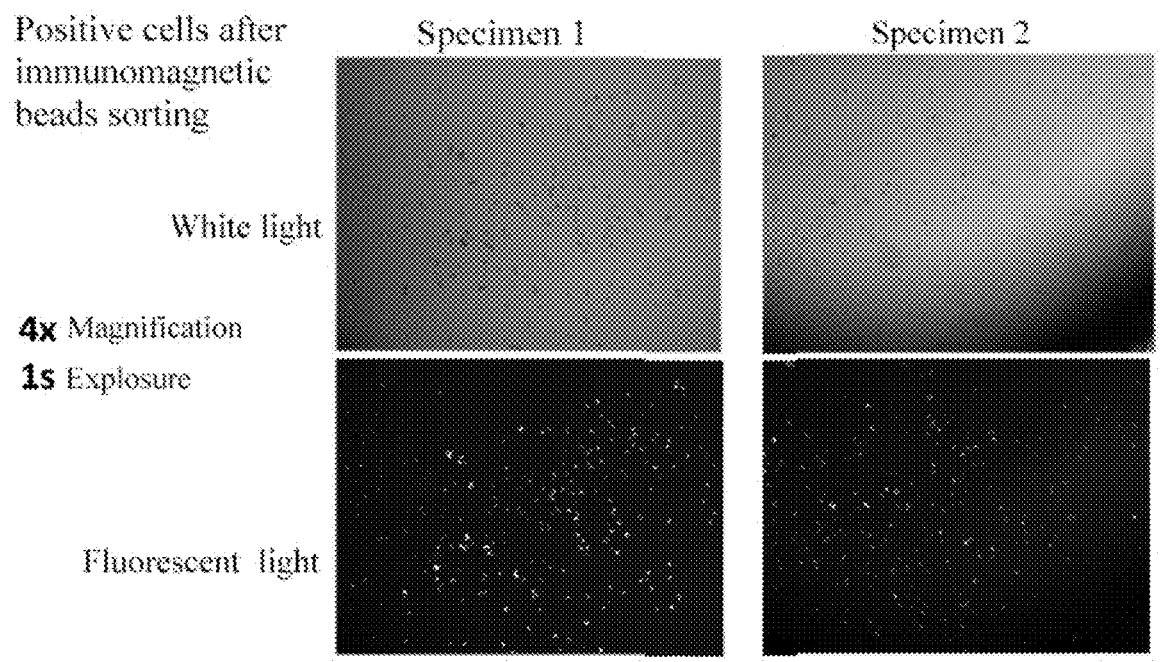
FIG. 16 is a picture showing positive cells sorted by the control method of immunomagnetic beads.

Comparison Between the Method for Isolating Trophoblast Cells from Cervical Exfoliated Cells of a Pregnant Woman Based on the Microfluidic Sorting Chip and the Method of Immunomagnetic Beads (I) Experimental Sample:
Two samples of cervical exfoliated cell sap from a humanized specimen detected by Hybribio Medical Laboratory.
(II) Immunomagnetic Beads Sorting Served as a Control Experiment to Compare the Differences of the Effects of the Two Methods.
The method of the present invention was the same as that in Example 2.
The process for sorting trophoblast cells by the immunomagnetic beads includes the following steps:
  step (1) the specimen of the collected cervical exfoliated cell of the pregnant woman was mixed well via oscillation for 5 min;
  step (2) the preserving solution was transferred into a 15 mL centrifugal tube, and 3 mL cell separating solution was added to the bottle of the preserving solution, and mixed evenly by oscillation, then the remaining solution was transferred into the same 15 mL centrifugal tube;
  step (3) the solution was centrifuged for 10 min at 3000 rpm and supernatant was discarded;
  step (4) 1 mL 1×PBST was added and mixed well and transferred to a 1.5 mL EP tube, and centrifuged for 5 min at 3000 rpm and supernatant was discarded;
  step (5) the step (4) was repeated twice;
  step (6) 200 μL 0.5% Triton X-100 was added and mixed well, then permeabilized at room temperature for 20 min;
  step (7) the step (4) was repeated for three times;
  step (8) 200 μl A primary antibody was added and mixed well, incubating over night at 4° C.;
  step (9) the step (4) was repeated for three times;
  step (10) 200 μl A secondary antibody was added and mixed well for reaction for 1 h at 37° C.;
  step (11) the step (4) was repeated for three times, and 200 μL buffer (DPBS+0.1% BSA+2 mM EDTA) was used for resuspending;
  step (12) 25 μl beads were fully mixed with 50 μl buffer well, and 600 g were centrifuged for 10 min, and supernatant was discarded, and the remaining solution was resuspended with 25 μl buffer, and then added to the mixed solution in the step (11);
  step (13) reaction was performed for 20 min at 2° C.-8° C.;
  step (14) 1 mL buffer was added and mixed well, standing on a magnetic frame for 2 min, then supernatant was discarded (200 μl was preserved for comparison);
  step (15) the step (14) was repeated for two to three times;
  step (16) 200 μl buffer preheated at 37° C. was added for resuspending, and 4 μl Release Buffer was added and mixed well;
  step (17) 15 min later at room temperature, the solution was pipetted for 5-10 times with a sample loading pipette, standing on the magnetic frame for 2 min, and supernatant was collected;
  step (18) 200 μl buffer was added and pipetted for 5-10 times, standing on the magnetic frame for 2 min, then supernatant was collected;
  step (19) the step (18) was repeated for three times to finally obtain the trophoblast cells.
(III) Result
The sorted positive cells were subjected to photo shooting with a SUNNY RX50 fluorescence microscope, as shown in FIGS. 14-16. FIG. 14 is a picture showing positive cells sorted by the method of the present invention; FIG. 15 is a picture showing comparison of positive cells and negative cells before and after being sorted by the method of the present invention; FIG. 16 is a picture showing positive cells sorted by the immunomagnetic beads. It can be obviously seen from the comparison that there is an obvious difference in the order of magnitudes of the cell population after being sorted by the two methods; the method of the present invention is significantly superior to the immunomagnetic beads. Statistics show that the number of positive cells sorted by the method of the present invention may be up to about 3000-13,000.

The examples described above are merely several embodiments of the present invention, and described more specifically, but may be not construed as limiting the scope of the patent invention. It should be indicated that a person skilled in the art may further make several deformations and improvements without departing from the concept of the present invention. Moreover, these deformations and improvements shall fall within the protection scope of the present invention. Therefore, the protection scope of the present invention shall be subjected to the claims attached.

What is claimed is:

1. A method for isolating trophoblast cells, the method comprising:
  step (1) preparing a sample cell suspension from a sample of cervical exfoliated cell sap, wherein the sample cell suspension is suspended in 1×PBS containing 0.2%-0.4% FBS;
  step (2) adding a specific antibody to the sample cell suspension for incubation, wherein a primary antibody is incubated in the following conditions: reacting for 30-90 minutes at 4° C.; and a second antibody-fluorescent labeling complex is incubated in the following conditions: reacting for 20 minutes at 2° C.-8° C.;
  wherein the specific antibody is an antibody combination corresponding to a specific antigen expressed on a surface of or an inside of corresponding trophoblast cells, and the antibody combination is HLA-G+CK7, HLA-G+CK18, HLA-G+β-HCG, CD31+HPL, MMP9+CD31, HLA-G+HPL, HLA-G+MMP9, HLA-G+CD31, HLA-G+P, CD31+P, HLA-G+CDH5, CD31+CDH5, CD31+CK7+HLA-G, HLA-G+CK18+CD31, HLA-G+β-HCG+CD31, CD31+HPL+HLA-G, MMP9+CD31+HLA-G, CD31+P+HLA-G or HLA-G+CDH5+CD31;

step (3) performing fluorescence labeling and microfluidics cell sorting of a cell resuspension incubated in the step (2) by a microfluidic sorting chip to obtain isolated and purified placental trophoblast cells;

wherein a liquid-phase cell sorting system is 0.2%-0.4% Triton-X-100;

the microfluidic sorting chip comprises a substrate and a cover plate fitted therewith;

wherein one side of the substrate is provided with a main runner, a side runner A and a side runner B, and the side runners A and B are respectively close to left and right end portions of the main runner;

and wherein another side of the substrate is provided with an inlet C, an inlet S, an outlet N and an outlet T; the inlets C and S and the outlets N and T penetrate the substrate to communicate with the side runners A and B on the other side; and a position of the inlet C corresponds to the left end portion of the main runner; a position of the inlet S corresponds to an end portion of the side runner A; a position of the outlet N corresponds to the right end portion of the main runner; and a position of the outlet T corresponds to an end portion of the side runner B;

and a deflection electrode device is further disposed in the main runner and at a convergence site of the outlet N and the outlet T; and each of the main runner, the side runner A and the side runner B has a width not greater than 1000 μm and a depth not greater than 500 μm.

2. The method according to claim 1, wherein the step (2) comprises: successively and specifically binding the primary antibody and the second antibody-fluorescent labeling complex to a target antigen step by step by incubation, wherein a washing and centrifugal separation technology is used to avoid cross contamination during the binding process.

3. The method according to claim 1, wherein the step (3) comprises: feeding the incubated cell resuspension into the inlet C of the microfluidic sorting chip, feeding a buffer solution into the inlet S, then placing the microfluidic sorting chip in a cell sorter to carry out a sorting program, and collecting specimens at the outlet T at the end of the sorting program to obtain sorted trophoblast cells.

* * * * *